(12) United States Patent
Licha et al.

(10) Patent No.: US 6,319,488 B1
(45) Date of Patent: Nov. 20, 2001

(54) CONTRAST MEDIUM FOR NEAR INFRARED DIAGNOSIS

(75) Inventors: Kai Licha; Björn Riefke; Werner Weitschiess; Dieter Heldmann; Violetta Sudmann, all of Berlin (DE)

(73) Assignee: Institut für Diagnostikforschung GmbH an der Freien Universität Berlin, Berlin (DE)

(*) Notice: Subject to any disclaimer, the term of this patent is extended or adjusted under 35 U.S.C. 154(b) by 0 days.

(21) Appl. No.: 09/051,511

(22) PCT Filed: Sep. 26, 1996

(86) PCT No.: PCT/DE96/01878

§ 371 Date: Apr. 9, 1998

§ 102(e) Date: Apr. 9, 1998

(87) PCT Pub. No.: WO97/13490

PCT Pub. Date: Apr. 17, 1997

(30) Foreign Application Priority Data

Oct. 11, 1995 (DE) .............................. 195 39 409

(51) Int. Cl.⁷ .............................. A61B 10/00; A61B 5/00; A61B 8/00
(52) U.S. Cl. .................. 424/9.6; 424/1.11; 424/1.65; 424/9.1; 548/100; 548/146
(58) Field of Search .............................. 424/1.11, 1.65, 424/9.1, 9.3, 9.4, 9.5, 9.6; 544/1, 3, 63, 50; 548/100, 146, 215, 300.1; 568/300, 303, 700; 546/152

(56) References Cited

U.S. PATENT DOCUMENTS

| 3,916,069 | * | 10/1975 | Tiers et al. | 428/411 |
|---|---|---|---|---|
| 5,494,793 | * | 2/1996 | Schindele et al. | 435/6 |

FOREIGN PATENT DOCUMENTS

| 266196 | * | 5/1988 | (EP) . |
| 266195 | * | 5/1998 | (EP) . |
| 89/10758 | * | 11/1989 | (WO) . |
| 92/07036 | * | 4/1992 | (WO) . |
| 95/08772 | * | 3/1995 | (WO) . |
| 96/17628 | * | 6/1996 | (WO) . |

OTHER PUBLICATIONS

Kitchell et al, 1985, Methods in Enzymology, vol. 112, pp. 436–449, Poly(lactic/glycolic acid) Biodegradable Drug-Polymer Matrix Systems.*

Riefke et al, 1996, SPIE Proceedings, vol. 2927, pp. 199–208, "In vivo characterization of Cyanine dyes as contrast agents for near infrared imaging".*

Beuthan et al, 1993, IR–Diaphanoscopy in Medicine, Medical Optical Tomography: Functional Imaging & Monitoring, vol. ISii, pp. 263–282.*

Scholes et al, Journal of Controlled Release, 25, pp. 145–153, The preparation of sub–200nm poly(lactide–c–o–glycolide) microspheres for site–specific drug delivery, 1993.*

Sanchez et al, European Journal of Pharmaceutics and Biopharmaceutics, vol. 41, No. 1, pp. 31–37, "Poly (D,L–lactide co–glycolide) Micro and Nano–spheres as a way to prolong Blood Plasma Levels of Subcutaneously Injected Cyclosporin A", 1995.*

Shen et al, Makromol. Chem., Rapid Commun., vol. 14, pp. 457–460, "Synthesis and characterization of poly DL–lactic acid/glycolic acid", 1993.*

Kohso et al, Endoscopy, vol. 22, pp. 217–220, "An investigation of an infrared Ray Electronic Endoscope with a Laser Diode Light Source", 1990.*

Ballai et al, Cancer Immunol. Immunother. vol. 41, pp. 257–263, "Tumor labeling in vivo using cyanine–conjugated monoclonal antibodies", 1995.*

Deligeorgiev et al, Dyes and Pigments, vol. 12, No. 2, pp. 157–162, "Near Infrared Absorbing Pyrylium Trimethine cyanine Dyes", 1990.*

Gadjev et al, Dyes and Pigments, vol. 14, No. 1, pp. 73–77, "Near–Infrared Absorbing Asymmetrical Trimethine Cyanine Dyes", 1990.*

Gadjev et al, Dyes and Pigments, vol. 17, No. 2, pp. 153–162, "Near Infrared Absorbing Asymmetric Trimethine Cyanine Dyes Containing BenZ [c,d] indolium and Pyrylium End Groups", 1991.*

Kuramoto et al, Dyes and Pigments, vol. 11, pp. 21–35, "Synthesis and Characterization of Deep–Coloured Squarylium Dyes for Laser Optical Recording Media", 1989.*

Terpetschnig, et al, Analytica Chimica Acta, vol. 282, pp. 633–641, Synthesis, spectral properties and photostabilities of symmetrical and unsymmetrical squaraines; a new class of fluorophores with long–wavelength excilation and emmision, 1993.*

Kuramoto, JSDC, vol. 106, pp. 181–186, The role of excited singlet molecular oxygen in the photodegradation of functional squarylium dyes, 1990.*

Slominskii et al, Ukrainskii Khimicheskii Zhurnal, vol. 40, No. 6, pp. 625–629, "Tricarbocyanines with Hydrocarbon Rings in the Chromophore", 1974.*

Makin et al, Organic Chemistry, vol. 23, No. 10, Part I, pp. 1850–1852, Chemistry of Enol Esters.LXXIX. Reaction of Glutaconaldehyde acetals and their derivatives with heterocyclics Compounds The Synthesis of Tricarbo–cyanine Dyes, 1987.*

* cited by examiner

Primary Examiner—Dameron L. Jones
(74) Attorney, Agent, or Firm—Wood, Phillips, VanSanten, Clark & Mortimer

(57) ABSTRACT

This invention relates to colloidal systems charged with polymethine dyes and having suitable photophysical and pharmacological properties, their use as a contrast medium in fluorescence and transillumination diagnostics in the near infrared spectral range, as well as methods for their production.

11 Claims, 1 Drawing Sheet

CONTRAST MEDIUM FOR NEAR INFRARED DIAGNOSIS

This application is a 371 of PCT/DE96/01878 filed Sep. 26, 1996.

FIELD OF THE INVENTION

This invention relates to colloidal systems charged with polymethine dyes, their use as a contrast medium in fluorescence and transillumination diagnostics in the near infrared spectral range, as well as methods for their production.

BACKGROUND OF THE INVENTION

As biological tissue has relatively high permeability for long-wave light in the range of 700 to 1000 nm, a diagnostician can therefore use a completely different method of tissue imaging in addition to advanced medical imaging techniques such as X-raying, magnetic resonance tomography, or ultrasonic diagnosis.

Tissue-specific information can be obtained both by detecting the non-absorbed portion of radiation by means of a transmission image, and by detecting fluorescence radiation emitted after exposing the tissue to light in the near infrared range.

The main problem with the use of near infrared radiation is the extraordinarily wide scattering of light, which yields only a rather blurred image of a clearly contoured object despite different photophysical properties of such an object and its environment. This problem intensifies the greater the distance from the surface and may be considered the major limiting factor of both transillumination and the detection of fluorescence radiation.

SUMMARY OF THE INVENTION

Suitable fluorescent dyes that accumulate in diseased tissue (particularly in tumours) and display a specific absorption and emission behaviour may contribute towards enhancing the distinction of healthy from diseased tissue. The change in the irradiated (scattered) light caused by absorbtion of the dye, or fluorescence induced by exciting radiation, is detected and provides the actual tissue-specific information.

Until now, photosensitizers designed for use in photodynamic therapy (PDT) (including porphyrins, chlorines, phthalocyanines, naphthalocyanines) have been used for localizing and visualizing tumours (Bonnett R. *New photosensitizers for the photodynamic therapy of tumours.* SPIE Vol. 2078, 1994). The classes of compounds listed here share the disadvantage that in the wavelength range of 600 to 1200 nm they are either not absorbing at all or to a very little extent only. The photosensitizing effect of these dyes is disturbing for purely diagnostic uses where no effects are desired. Furthermore, photostability of the dyes listed here often is quite low.

In contrast to this, the absorption and fluorescent behaviour of dyes from the class of polymethines is characterized by high absorption coefficients in the range between 700 and 1000 nm and a sufficient fluorescent quantum yield. The photosensitizing effect of polymethines can be neglected, and most of them are highly photostable.

A clear change in the pharmacokinetic properties of fluorescent dyes may be achieved by transforming them into colloidal systems. As a result, a tissue or organ-specific, or location-specific accumulation of the fluorescent dyes formulated in this way may be achieved.

Furthermore, the dyes must be strongly hydrophilic to be applied in an aqueous solution so that sufficient quantities of dye for imaging can be introduced into the body using a water solution.

It is known that the transformation of dyes into colloidal systems may increase the applicable dose.

It is an object of this invention to provide a contrast medium that accumulates to a considerable extent in the tissues to be examined and can be detected in said tissues using near infrared radiation.

DETAILED DESCRIPTION OF THE PREFERRED EMBODIMENTS

Figure 1:
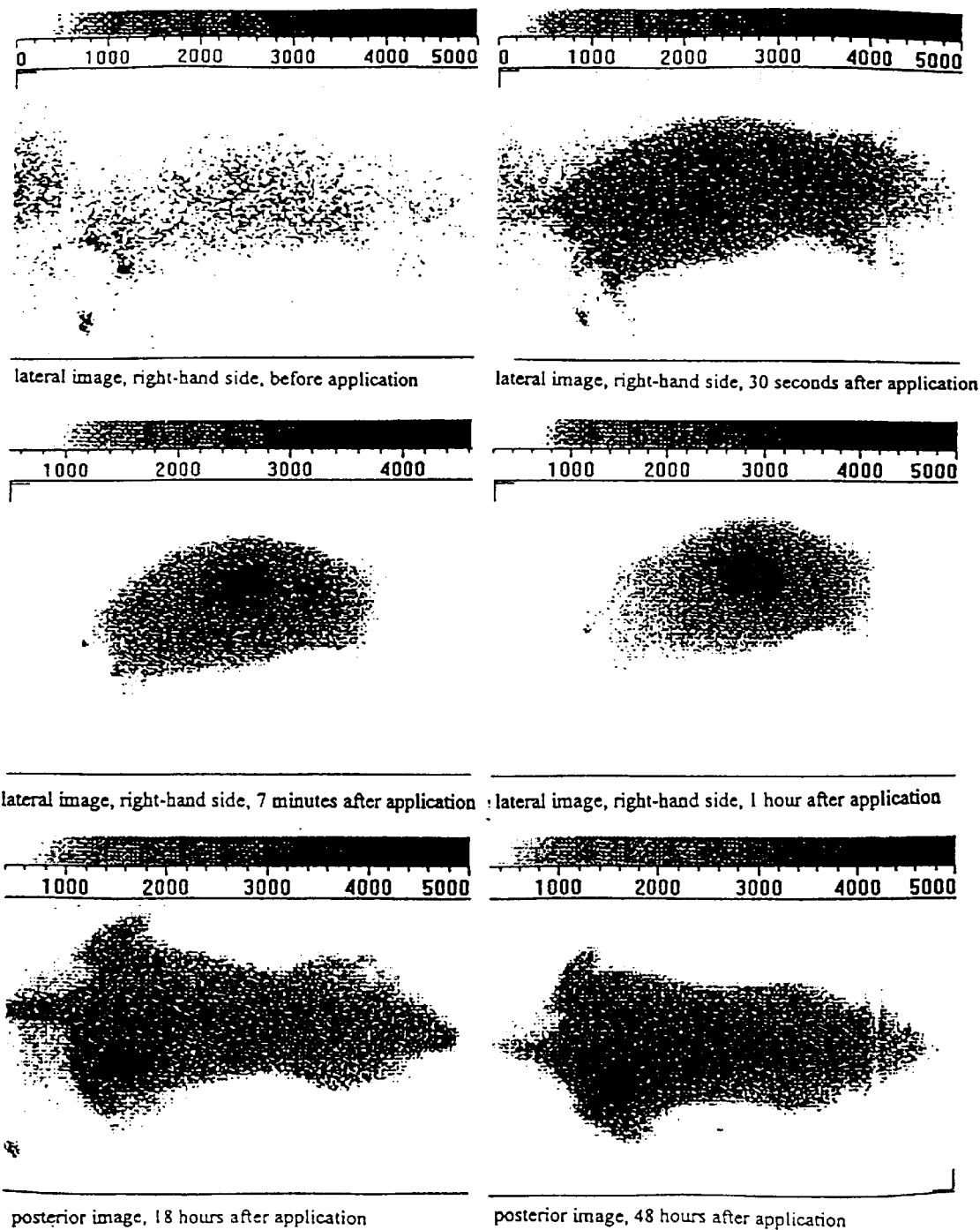
FIG. 1 depicts fluoroscopic imaging of a nude mouse with an LS174T tumour after application of a contrast medium according to the present invention.

This problem is solved according to the invention by providing contrast media containing colloidal systems charged with dye, said colloids having sizes from 5 nm to 10 $\mu$m and containing a minimum of one dye that absorbs and/or fluoresces in a wavelength range from 600 to 1200 nm. For a definition of colloids, see Hunnius, *Pharmazeutisches Wörterbuch*, 6th edition, Berlin: de Gruyter 1986, pp. 589 f.; this description, however, includes coarsely dispersed systems with particle sizes up to 10 $\mu$m in the concept of colloidal systems.

Surprisingly, it was found that colloidal systems charged with dye accumulate in local inflammation or tumor areas. This accumulation is excellently suited for visualizing tumours or inflammations using NIR diagnosis.

Furthermore, it was surprisingly found that the contrast media of the invention are quickly degraded in specific cells, for example, in Kupfer cells of the liver, which results in a rapid decrease of colloid concentrations in the blood, while the colloid particles already absorbed by the target tissue are degraded at a much slower pace. This reduces the background noise caused by the concentration of contrast medium in the blood, which improves the visualization of lesions and/or makes them visible at an earlier stage.

This invention thus relates to colloid systems charged with dye and containing colloidal particles of sizes between 5 nm and 10 $\mu$m with dye molecules integrated in, adhering to, or encapsuled by their walls and/or cavities.

Suited are all systems in which the dyes are integrated in colloidal particles consisting of biodegradable, partially synthetic materials or materials identical with natural substances. The properties and methods of preparing suitable colloidal particles are described, for example, in Boyett, J. B., and Davis, C. W. *Injectable Emulsions and Suspensions.* In: Liebermann, H. A., M. M. Rieger, and G. S. Banker, eds. *Pharmaceutical Dosage Forms: Disperse Systems.* Vol. 2. New York: Marcel Dekker, 1988, 379–416.

Particularly suitable are systems in which the synthetic polymeric material has been selected from the following group: Poly-$\epsilon$-caprolactone, polylactic acid, polyglycolic acid, and mixed polymers from polylactic and polyglycolic acid, polyhydroxy butyric acid, polyhydroxy valeric acid, and mixed polymers from polyhydroxy butyric acid and polyhydroxy valeric acid, polyamino acids, polyalkyl cyanoacrylates, polyamides, polyacrylodextrane, polyacrylic starch, polyacrylosaccharide, polyacrylamide, polyester, poly(ortho)ester, polyphosphorenes, and copolymers of lactic acid and/or glycolic acid and polyoxyethylene. Preferred natural or partially synthetic biodegradable polymeric materials primarily include proteins such as albumins, collagen, gelatin, haemoglobin or fibrinogen and starches, dextranes, chitin and chitosan.

Particularly suitable are also amphiphilic substances that either encapsule the fluorescent dye in colloidal particles or form colloidal particles together with the fluorescent dye. Preferred substances are phospholipids, fatty acids, fatty alcohols, cholesterol, esters or ethers of fatty alcohols or fatty alcohols and fatty acids, sugar derivatives with fatty acids or polyoxyethylene, esters or ethers of phospholipids, fatty acids, fatty alcohols with polyoxyethylene, bile acids, derivatives of sorbitan with polyoxyethylene or fatty acids or fatty alcohols as well as their combinations.

Preferred contrast media according to the invention contain colloids from proteins such as albumins, collagen, gelatin, haemoglobin or fibrinogen, or starches and starch derivatives, dextranes, chitin, or chitosan.

Other preferred contrast media according to the invention contain colloids from phospholipids, fatty acids, fatty alcohols, cholesterol, esters of fatty alcohols and fatty acids, ethers of fatty alcohols and fatty acids, sugar derivatives containing fatty acids or polyoxyethylene, esters or ethers of phospholipids, fatty acids or fatty alcohols with polyoxyethylene, bile acids, derivatives of sorbitan with polyoxyethylene, fatty acids or fatty alcohols, and combinations of said substances.

Particularly preferred are such contrast media of the invention that contain polyesters of α-, β-, γ- or ε-hydroxycarboxylic acids, polyalkyl cyanoacrylates, polyamino acids, polyamides, polyacrylated saccharides or poly(ortho)esters in the form of colloids.

The dyes used for the colloidal near-infrared diagnostic agent are characterized by the fact that they absorb and fluoresce in a wavelength range of 600 to 1200 nm, have absorption coefficients of about 100,000 1 $mol^{-1}$ $cm^{-1}$ and higher, and, inasmuch as fluorescence is desirable, show fluorescence quantum yields of more than 5%.

The dyes used are of the class of polymethine dyes selected from the following group: cyanine, styryl, merocyanine, squaraine, and oxonol dyes.

Preferred are dyes of the class of cyanine dyes having maximum absorption and fluorescence values between 700 and 1000 nm and extinction coefficients of about 140,000 1 $mol^{-1}$ $cm^{-1}$ and more, and carrying one or several unsubstituted, branched or non-branched, acyclic or cyclic or, optionally, aromatic carbon-hydrogen residues and/or containing oxygen, sulfur, nitrogen.

The contrast media of the invention contain a cyanine, styryl, merocyanine, squaraine, or oxonol dye, or a mixture of said dyes.

Preferred are contrast media according to the invention that contain a dye from the class of cyanine or squaraine dyes.

Also preferred are contrast media according to the invention in which the dye carries one or several additional, branched or non-branched, cyclic or polycyclic alkyl, alkenyl, polyalkenyl, alkinyl, polyalkinyl, aryl, alkylaryl or arylalkyl residue(s), each containing up to 60 carbon atoms, and optionally carrying additional halogen atoms, hydroxy, carboxy, aminocarbonyl, alkoxycarbonyl, amino, aldehyde, oxo, oxy, or alkoxy groups that contain up to 20 carbon atoms, and/or may be interrupted and/or replaced by one or several heteroatoms of the O, N, S, or P series.

Particularly preferred are contrast media of the invention that contain at least one dye of the general formula I, II, or III

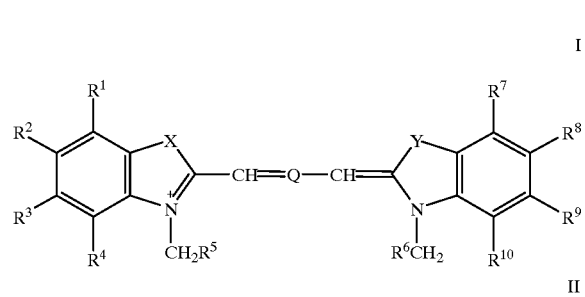

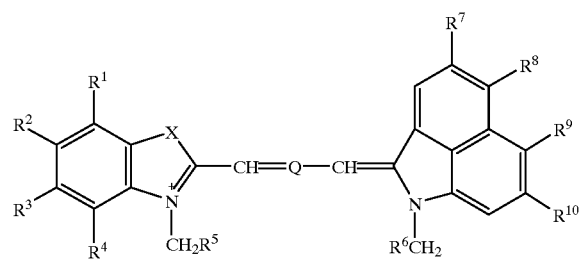

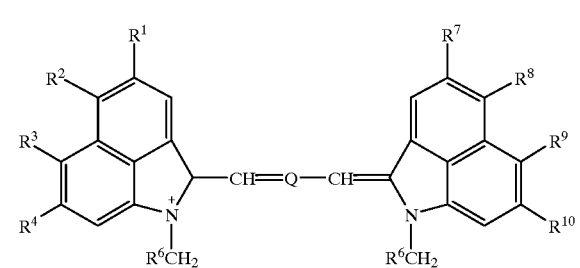

wherein
$R^1$, $R^2$, $R^3$, $R^4$, $R^7$, $R^8$, $R^9$, and $R^{10}$ are the same or different, and each of which independently represents a —$COOE^1$, —$CONE^1E^2$, —$NHCOE^1$, —$NHCONHE^1$, —$NE^1WE^2$, —$OE^1$, —$SO_3E^1$, —$SO_2E^1$, —$SO_2NE^1E^2$, —$E^1$ residue, a fluorine, chlorine, bromine, or iodine atom or a nitro group, or where 5- to 6-membered rings are anellated to each pair of adjacent residues $R^1$, $R^2$, $R^3$, or $R^4$, $R^7$, $R^8$, $R^9$ or $R^{10}$ respectively, depending on the C atoms located in between, said rings being either saturated or unsaturated or aromatic and optionally carrying additional —$COOE^1$, —$CONE^1E^2$, —$NHCOE^1$, —$NHCONHE^1$, —$NE^1E^2$, —$OE^1$, —$SO_3E^1$, —$SO_2E^1$, —$SO_2NE^1E^2$ residues, wherein
$E^1$ and $E^2$ are same or different, each of which independently represents a hydrogen atom, a saturated or unsaturated, branched or non-branched $C_1$–$C_{50}$ alkyl chain, and said chain or parts thereof optionally forms a cyclic $C_5$–$C_6$, or a bicyclic $C_{10}$ unit interrupted and/or replaced by oxygen atoms, sulfur atoms, nitrogen atoms, carboxylic acid ester, carboxylic acid amide, urea, thiourea, carbamate or ether groupings, or represent a hydroxypolyoxyethylene or methoxypolyoxyethylene chain or a branched or non-branched $C_1$–$C_{10}$ alkyl chain substituted with 1 to 19 fluorine atoms, $R^5$ and $R^6$ independently represent an —$E^1$ residue or a $C_1$–$C_4$ sulfoalkyl chain, where E1 is as defined above Q represents a

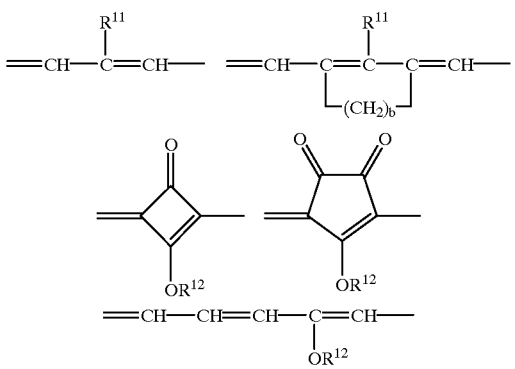

fragment
wherein
$R^{11}$ is a hydrogen, fluorine, chlorine, bromine, or iodine atom, a —$NE^1E^2$, —$OE^1$, or —$E^1$ residue or a nitro group,
$R^{12}$ represents a hydrogen atom or an —$E^1$ residue,
b is one of the numbers 0, 2 or 3,
where $E^1$ and $E^2$ are as defined above,
X and Y are same or different, each of which independently represents O, S, —CH=CH—, or a

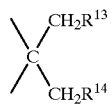

fragment,
wherein
$R^{13}$ and $R^{14}$ independently represent hydrogen, a saturated or unsaturated, branched or non-branched $C_1$–$C_{15}$ alkyl chain, and where the residues $R^{13}$ and $R^{14}$ may be interconnected by forming a 5- or 6-membered ring, said members being interrupted and/or replaced by oxygen atoms and/or hydroxy groups, alkoxy groups containing up to 6 carbon atoms, carboxylic acid ester and/or carboxylic acid amide units,
or their carboxylic acid and/or sulfonyl salts with physiologically tolerable inorganic or organic cations.

Sodium, potassium, calcium, magnesium, gadolinium, and lysine, glutamine and methyl glutamine may occur as cations.

Dyes with a positive total charge are preferably iodides, bromides, or perchlorates.

The contrast media according to the invention may furthermore contain a minimum of two dyes having different photophysical and/or pharmacological properties.

The contrast media according to the invention may furthermore contain adjuvants, substrates, and diluents common in galenics.

The dyes are prepared using methods known from the relevant literature as, for example, Hamer, F. M. *The Cyanine Dyes and Related Compounds*. New York: John Wiley and Sons, 1964; *Bioconjugate Chem.* 4 (1993), 105–11; *Anal. Biochem.* 217 (1994), 197–204; *Tetrahedron* 45 (1989), 4845–66; *Anal. Chim. Acta* 282 (1993), 633–641; *Dyes Pigm.* 21 (1993), 227–234; EP 0 591 820 A1.

Another object of this invention is the use of the contrast media of the invention for in vivo fluorescence and absorption diagnosis in the near infrared range.

In vivo diagnosis using the contrast media of the invention is preferably carried out after intravenous administration of the substances by irradiating with monochrome light of a wavelength range of 600 to 1200 nm and position-dependent detection of non-absorbed radiation and/or fluorescent radiation. A synthetic image is generated based on the data obtained.

The diagnostic agent of the invention is prepared in analogy with the methods for the production of colloidal particles described in the relevant literature in which one or several dye(s) is/are added to the reaction mixture. The charging ratio can be varied by setting the reaction system to another dye concentration.

The preferred method is to dissolve the organic materials described above together with one or more dyes in one or several organic solvent(s) that cannot be mixed with water, and to emulgate them after optionally adding another solvent, an emulsifying agent may optionally be added to the emulsion. The colloidal system obtained can subsequently be filtered and stabilized by drying, e.g. by lyophilizing.

These contrast media are also manufactured according to methods known to an expert skilled in the art which may involve the use of common adjuvants and/or diluents, and the like. This includes physiologically tolerable electrolytes, buffers, detergents, emulgators, and substances used to adjust osmolality or to enhance the stability and solubility of the contrast media, e.g. cyclodextrines. The sterility of the preparations during the manufacturing process and, above all, when applying them, is to be ensured by common pharmaceutical measures.

The following examples shall explain the invention in some more detail.

EXAMPLE 1

Production of a Particle Suspension Containing 1,1',3,3,3',3'-hexamethyl Indotricarbocyanine Iodide 7.6 mg of hexamethyl indotricarbocyanine iodide and 0.2 g of a copolymer of lactic acid and glycolic acid having a molecular mass of about 15,000 g/mol are dissolved in 2.5 ml of methylene chloride. This solution is added under vigorous stirring to 20 ml of a 2% solution of gelatin that has been autoclaved for 15 minutes at 121° C. The mixture is kept agitated for another 45 minutes. The suspension thus obtained is filled into 20 ml glass vessels in portions of 5 ml and frozen directly using liquid nitrogen. Subsequently, the frozen suspension is lyophilized. After re-suspending a portion with 5 ml of a 0.9% solution of common salt, the suspension contains about $10^{10}$ particles containing hexamethyl indotricarbocyanine iodide per ml with particle sizes from about 1 to 10 μm.

EXAMPLE 2

Application of the Preparation from Example 1

Fluoroscopic imaging of a nude mouse with a LS174T tumour after applying 200 μl of a poly-(1-lactide-glycolide) particle suspension ($10^{10}$ particles/ml) with encapsuled hexamethyl indotricarbocyanine iodide (0.6 μmol/ml) using a CCD camera yielded images showing fluorescence mainly in the tumour tissue after 24 hours (FIG. 1).

What is claimed is:
1. An in vivo contrast medium and target tissue combination, wherein said target tissue is selected from the group consisting of inflamed tissue and tumor tissue, said in vivo contrast medium comprising a colloidal system with particles having a size range from 5 nm to 10 μm, said colloidal system further comprising at least one dye fluorescing in the wavelength range from 600 nm to 1200 nm upon direct absorption of monochromatic light in the wavelength range from 600 nm to 1200 nm, said at least one dye is selected from the group consisting of the general formula I,

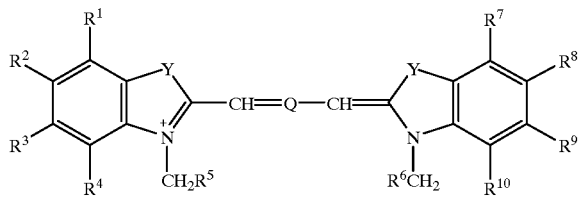

wherein
$R^1$–$R^{10}$ represent the residue $E^1$, where $E^1$ is a hydrogen, wherein
Q is one of the following fragments:

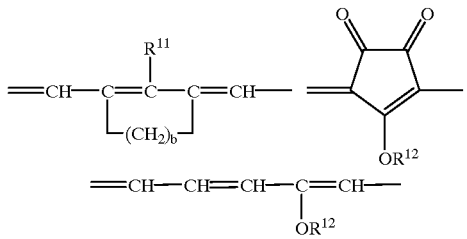

wherein
b=0,
$R^{11}$ represents a hydrogen atom,
$R^{12}$ represents a hydrogen atom or a saturated or unsaturated, branched or non-branched $C_1$–$C_{50}$ alkyl chain, and said chain or parts thereof form a cyclic $C_5$–$C_6$, or a bicyclic $C_{10}$ unit interrupted and/or replaced by oxygen atoms, sulfur atoms, nitrogen atoms, carboxylic acid ester, carboxylic acid amide, urea, thiourea, carbamate, ether groupings, or represent a hydroxypolyoxyethylene or methoxypolyoxyethylene chain or a branched or non-branched $C_1$–$C_{10}$ alkyl chain substituted with 1 to 19 fluorine atoms,
where X and Y are both

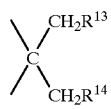

fragment,
and wherein
$R^{13}$ and $R^{14}$ independently represent hydrogen.

2. The contrast medium according to claim 1, characterized in that the colloids contain proteins such as albumins, collagen, gelatin, haemoglobin or fibrinogen, or starches, dextranes, chitin or chitosan.

3. The contrast medium according to claim 1, characterized in that the colloids contain phospholipids, fatty acids, fatty alcohols, cholesterol, esters of fatty alcohols and fatty acids, ethers of fatty alcohols, sugar derivatives with fatty acids or polyoxyethylene, esters or ethers of phospholipids, fatty acids, or fatty alcohols with polyoxyethylene, bile acids, derivatives of sorbitan with polyoxyethylene, fatty acids, or fatty alcohols, as well as combinations of said substances.

4. The in vivo contrast medium according to claim 1, wherein said at least one dye further comprises at least two dyes of general formula I.

5. The in vivo contrast medium according to claim 1, wherein said in vivo contrast medium farther comprises at least one adjuvant, at least one substrate, and at least one diluent common in galenics.

6. A method for in vivo near infrared diagnosis of target tissue in an organism using an in vivo contrast medium capable of absorption and/or fluorescence in the 600 nm to 1200 nm wavelength range, said target tissue is selected from the group consisting of inflamed tissue and tumor tissue, said method comprising the steps of:

(a) preparing an in vivo contrast medium comprising a colloidal system, said colloidal system having a particle size range from 5 nm to 10 μm, said colloidal system comprising at least one dye, said at least one dye absorbs and/or fluoresces in the wavelength range from 600 nm to 1200 nm, said in vivo contrast medium being amenable to accumulation in said target tissue, said in vivo contrast medium being amenable to degradation by liver tissue at a faster rate than degradation by said target tissue;

(b) performing intravenous administration of said in vivo contrast medium into an organism;

(c) sufficiently irradiating said organism with monochrome light of a wavelength range of about 600 nm to 1200 nm to cause said in vivo contrast medium to fluoresce; and (d) scanning said irradiated organism using a CCD camera to obtain images of said in vivo contrast medium to detect the diseased tissue.

7. The method of claim 6 further comprising repeating steps (c) and (d) about 10 minutes after step (a), 1 hour after step (a), 18 hours after step (a), and 24 hours after step (a).

8. An in vivo contrast medium and target tissue combination, wherein said target tissue is selected from the group consisting of inflamed tissue and tumor tissue, said in vivo contrast medium comprising a colloidal system, said colloidal system having a particle size range from 5 nm to 10 μm, said colloidal system comprising a dye, said dye absorbing and/or fluorescing in the wavelength range from 600 nm to 1200 nm, said dye is 1,1',3,3,3',3'-hexamethyl indotricarbocyanine iodide of Example 1.

9. A method for imaging tumor tissue comprising the steps of:

(a) performing intravenous administration of an in vivo contrast medium into a body suspected of harboring tumor tissue, said in vivo contrast medium comprising colloidal system with a particle size range from 5 nm to 10 μm, said colloidal system comprising one or more dyes, said one or more dyes absorbing and/or fluorescing in the wavelength range from 600 nm to 1200 nm, said in vivo contrast medium being amenable to accumulation in said tumor tissue, said in vivo contrast medium being amenable to degradation by liver tissue at a faster rate than degradation by said tumor tissue;

(b) irradiating said body with monochrome light in the wavelength range of about 600 nm to 1200 nm to cause said in vivo contrast medium of step (b) to absorb and/or fluoresce; and (c) scanning said irradiated body to yield images of said tumor tissue in said body.

10. The method of claim 9, wherein step (c) further comprises using a CCD camera to provide images of said tumor tissue.

11. The method of claim 9, wherein said body is selected from the group comprising of a human patient and an animal in possession of a liver.

* * * * *